United States Patent [19]

Ley et al.

[11] 3,980,779

[45] Sept. 14, 1976

[54] 3-AMINO-1,2,4-BENZOTRIAZINE-1,4-DI-N-OXIDE COMPOSITIONS AND METHOD OF USING SAME

[75] Inventors: Kurt Ley, Odenthal-Globusch; Florin Seng, Schildgen; Karl Georg Metzger, Wuppertal-Elberfeld, all of Germany

[73] Assignee: Bayer Aktiengesellschaft, Germany

[22] Filed: Apr. 29, 1974

[21] Appl. No.: 465,165

Related U.S. Application Data

[62] Division of Ser. No. 326,389, Jan. 24, 1973, Pat. No. 3,868,371.

[30] Foreign Application Priority Data

Feb. 1, 1972   Germany............................ 2204574

[52] U.S. Cl. ................................................. 424/249
[51] Int. Cl.² .......................................... A61K 31/53

[58] Field of Search ..................................... 424/249

[56] References Cited
UNITED STATES PATENTS

| 3,482,024 | 12/1969 | Molnar et al. ...................... 424/249 |
| 3,562,270 | 2/1971 | Wagner-Jauregg et al. ......... 424/249 |

OTHER PUBLICATIONS

Mason et al., J. Chem. Soc, (B), 1970, pp. 911–916.

*Primary Examiner*—Frederick E. Waddell

[57]    ABSTRACT

Pharmaceutical compositions comprising a 3-amino-1,2,4-benzotriazine-1,4-di-N-oxide as the active ingredient and method of using same. Said compositions exhibit antimicrobial activity and may be used to promote livestock growth by adding an effective amount of said composition to edible fodder.

34 Claims, No Drawings

3-AMINO-1,2,4-BENZOTRIAZINE-1,4-DI-N-OXIDE COMPOSITIONS AND METHOD OF USING SAME

This is a division of application Ser. No. 326,389 filed Jan. 24, 1973 which issued on Feb. 25, 1975, as U.S. Pat. No. 3,868,371.

DETAILED DESCRIPTION

The present invention pertains to the novel compounds of the formula:

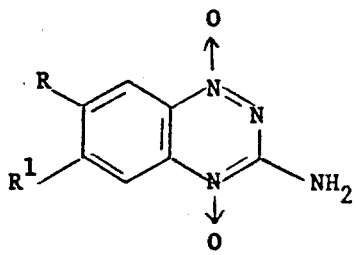

I wherein one of R and $R^1$ is hydrogen, halogeno, lower alkyl, halo(lower alkyl), lower alkoxy, carbamyl, sulfonamido, carboxy or carbo(lower alkoxy) and the other of R and $R^1$ is halogeno, lower alkyl, halo(lower alkyl), lower alkoxy, carbamyl, sulfonamido, carboxy or carbo(lower alkoxy).

The foregoing compounds demonstrate antimicrobial activity and are useful in combatting, both prophylactically and therapeutically, infections of microbiological origin.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec.butyl, tert.butyl, pentyl, isopentyl, neopentyl, tert.pentyl, hexyl, and the like.

The term lower alkoxy denotes a straight or branched hydrocarbon chain bound to the remainder of the molecule through an ethereal oxygen atom as, for example, methoxy, ethoxy, propoxy, isopropoxy, butoxy, isobutoxy, pentoxy and hexoxy.

The term halogen denotes the substituents fluoro, chloro, bromo and iodo.

The present invention also embraces the method of combatting microbial infections in animals through administration of pharmaceutical compositions in which a pharmaceutical carrier is combined with an antimicrobially effective amount of a compound of the formula:

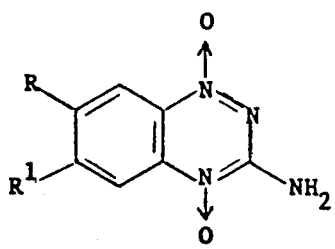

IA wherein R is hydrogen, halogeno, lower alkyl, halo(lower alkyl), lower alkoxy, carbamyl, sulfonamido, carboxy or carbo(lower alkoxy) and $R^1$ is hydrogen, halogeno, lower alkyl, halo(lower alkyl), lower alkoxy, carbamyl, sulfonamido, carboxy or carbo(lower alkoxy).

The compounds of Formula LA are also useful in livestock growth promoting compositions in which the compound is combined with an edible, fodder compatible carrier.

While it has been reported that condensation of o-nitroaniline and cyanamide with subsequent hydrogen peroxide oxidation of the reaction product yields 3-amino-benzo-1,2,4-triazine-di-N-oxide; see e.g. Mason et al., J. Chem. Soc., London, B 1970, 911, this process suffers from a number of disadvantages. Thus the product of the condensation has to be oxidized with hydrogen peroxide, which entails relatively high risks, especially in an industrial process, and produces the product in poor purity and yield. The compound itself appears to be largely of academic interest and no use is known for it.

The compounds of, and utilized in, the present invention are on the other hand advantageously prepared through the reaction of a benzofuroxan of the formula:

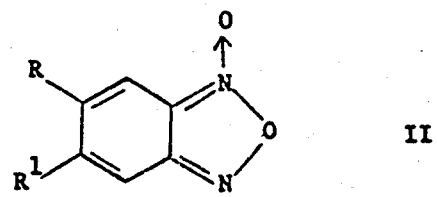

II which can also be depicted as

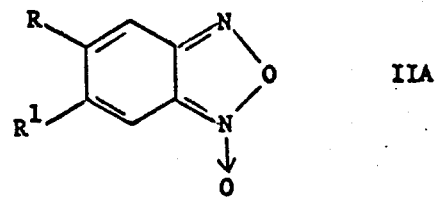

IIA and in which each of R and $R^1$ is hydrogen, halogeno, lower alkyl, halo(lower alkyl), lower alkoxy, carbamyl, sulfonamido, carboxy or carbo(lower alkoxy), with a salt of cyanamide followed by acidification of the reaction product. The cyanamide salt can be introduced as such or can be generated in situ through use of cyanamide in the presence of a base. A polar solvent as for example a liquid alkanol of 1 to 4 carbon atoms such as methanol, ethanol, propanol, butanol and the like, liquid alkanonitriles such as acetonitrile, ethers such as ethyl ether, dioxane and tetrahydrofuran and liquid amides such as dimethylformamide can be employed. Water and mixtures of these organic solvents with water, can also be used. The cyanamide or cyanamide salt can be in any desired form, but is preferably employed as an aqueous solution containing for example 50% by weight of cyanamide. Salts of cyanamide which include the alkali metal salts and alkaline earth metal salts, such as calcium, sodium and potassium salts, can be used. The use of disodium cyanamide is particularly preferred. When free cyanamide is employed, the reaction is performed in the presence of an inorganic and organic base or mixtures thereof such as the alkali metal alcoholates of lower alkanols, as for example sodium methoxide, potassium ethoxide and potassium t-butoxide. Examples of inorganic bases include the oxides, hydroxides and carbonates of such alkali metals and alkaline earth metals as calcium, magnesium, sodium and potassium; e.g.; calcium oxide, magnesium oxide, calcium carbonate, sodium hydroxide, potassium hydroxide, sodium carbonate and potassium carbonate. Preferred organic bases are quaternary ammonium hydroxides, as for example trimethylbenzylammonium hydroxide and tetramethylammonium hydroxide. When the salts of cyanamide are used, the addition of a base is not necessary. The reaction is carried out at temperatures of from about 0° to about 180°C, preferably from about 10° to about 100°C, and generally from about 20° to about 70°C. The reaction can be performed at elevated pressure but in general, normal pressures are used. From 1 to 10, especially 1.5 to 5, moles of cyanamide salt are employed per 1 mole of benzofuroxan. When free cyanamide is used, at least a stoichiometric amount of base is added. The process of the invention is typically carried out as follows. The benzofuroxan is suspended or dissolved in the solvent and the cyanamide salt, or cyanamide and base are added. After warming, if necessary, the salt of the desired 3-aminobenzo-1,2,4-triazine-di-N-oxide in most cases precipitates and can be isolated in the customary manner, as for example by filtration. Acidification of the isolated salt, or the reaction mixture if the salt does not precipitate, with an organic acid or inorganic aqueous acid such as for example acetic acid, hydrogen halide such as hydrochloric, hydrobromic and hydriodic acid; sulfuric acid and the like, liberates the final product which is isolated by conventional methods, as for example by filtration. The product may also be purified in the customary manner, such as by recrystallization. Dimethylformamide is a suitable recrystallization solvent.

The benzofuroxan starting material is symmetrical with regard to the 5- and 6-positions and thus the 5-substituted starting materials are identical with the 6-substituted compounds. If the benzofuroxan carries a substituent in one of the 5- or 6-positions or different substituents in the 5-position and 6-position, two isomers are obtained, one in which one substituent is in the 6-position and the other in the 7-position and a second in which the substituents are reversed in the 6- and 7-positions.

The isomer mixture can, if desired, be separated into their isomers through conventional techniques, as for example by chromatography but since both isomers demonstrate equivalent antimicrobial activity, there is no need to perform this step.

The compounds thus produced display strong antibacterial effects. Their effectiveness extends both to Gram positive and to Gram negative bacteria, such as Enterobacteriaceae, as for example Escherichia such as *Escherichia coli;* Klebsiella such as *Klebsiella pneumoniae;* Proteus such as *Proteus vulgaris, Proteus mirabilis, Proteus morganii* and *Proteus rettgeri;* Salmonella, especially *Salmonella typhimurium* and *Salmonella enteritidis;* Pseudomonadaceae such as *Pseudomonas aeruginosa;* Aeromonas such as *Aeromonas liquefaciens;* Clostridia such as *Clostridium botulinum* and *Clostridium tetani;* Micrococcaceae such as *Staphylococcus aureus* and *Staphylococcus epidermidis;* Streptococcaceae such as *Streptococcus pyogenes* and *Streptococcus faecalis* (Enterococcus); and Mycoplasmataceae such as *Mycoplasma pneumoniae* and *Mycoplasma arthritidis;* Mycobacteraceae such as *Mycobacterium tuberculosis* and *Mycobacterium leprae.*

The excellent and broad anti-bacterial activity of these compounds permits their use in the prevention and treatment of systemic and local bacterial infections in animals in both human and veterinary medicine. The compounds can also be used as fodder additives for promoting the growth and improving the fodder utilization in animal husbandry, especially in raising livestock such as for example, cattle, pigs, poultry and the like where they are administered via the fodder or drinking water or in fodder concentrates and in vitamins and/or preparations containing mineral salts. Mixing with the fodder or the fodder concentrates and the remaining fodder preparations is optionally carried out in the form of a premix.

The present invention also comprises pharmaceutical compositions which contain a major or minor amount, e.g. from 95 to 0.5%, of at least one 3-amino-1,2,4-benzotriazine-1,4-di-N-oxide of Formula IA in combination with a pharmaceutical carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e. physically discrete units containing a predetermined amount of the drug corresponding to a fraction or multiple of the dose which is calculated to produce the desired therapeutic response. The dosage units can contain one, two, three, four or more single doses or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the daily dose will be from about 5 to about 150 mg/kg and more commonly from about 25 to about 75 mg/kg of body weight. In some instances a sufficient therapeutic effect can be obtained at a lower dose while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low melting water soluble or insoluble solids such as polyethylene glycol, cocoa butter, higher esters as for example myristyl palmitate, or mixtures thereof.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellants such as the chlorofluorohydrocarbons.

The antimicrobial activity of these compounds can be conveniently observe in in vitro and in vivo models. For example, their minimum inhibitory concentration (MIC) can be determined in the plate test on a complete nutrient base of the following composition: 10 g of proteose-peptone, 10 g of veal infusion, 2 g of dextrose, 3 g of sodium chloride, 2 g of disodium phosphate, 1 g of sodium acetate, 0.01 g of adenine sulfate, 0.01 g of guanine hydrochloride, 0.01 g of uracil, 0.01 g of xantine, 12 g of agar-agar and 1 liter of water. With an incubation temperature of 37°C and an incubation time of 24 hours, the following typical values can be observed:

| MIC in γ/ml of Nutrient Medium | | | |
|---|---|---|---|
| | | Compound* | |
| Organism | A | B | C |
| Streptococcus pyogenes W | 32 | 8 | 4 |
| Staphylococcus aureus 133 | 16 | 8 | 4 |
| E. coli C 165 | 4 | 8 | 2 |
| E. coli A 261 | 4 | 8 | 2 |
| Pseudomonas aeruginosa W | 64 | 128 | 64 |
| Pseudomonas aeruginosa BONN | 8 | 128 | 32 |
| Proteus vulgaris 1017 | 2 | 4 | 1 |
| Klebsiella 63 | 4 | 8 | 2 |
| Klebsiella 8085 | 2 | 1 | 1 |

*Compound A = 3-amino-1,2,4-benzotriazine-1,4-di-N-oxide
Compound B = isomeric mixture of 6-chloro- and 7-chloro-3-amino-1,2,4-benzotriazine-1,4-di-N-oxide
Compound C = isomeric mixture of 6-methoxy and 7-methoxy-3-amino-1,2,4-benzotriazine-1,4-di-N-oxide The above in vitro data are confirmed in in vivo infections. Thus subcutaneous administration to white mice 15 minutes before intraperitoneal infection gives ED$_{50}$ 24 hours later of 20 and 25 mg/kg for compounds A and C, respectively, against *E.coli* C 165 and 250 and 40 mg/kg for compounds B and C, respectively, against *Staphylococcus aureus* 133.

The following examples will serve to further typify the nature of the present invention without being a limitation on the scope thereof.

EXAMPLE 1

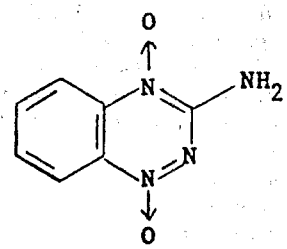

To a suspension of 13.6 g (0.1 mol) of benzofuroxan in a mixture of 40 ml of methanol and 40 ml of water at approximately 20°C are added in portions 17.2 g (0.2 mol) of disodium cyanamide. In the course of addition, the temperature rises to about 50-60°C and the solution assumes a blue-violet color. It is stirred for a further 40 minutes at about 60°C and the precipitate which separates out is then removed by filtration from the mother liquor, which is retained and processed further as described below. The precipitate is dissolved in water, the solution is filtered and the filtrate is acidified with acetic acid, whereupon 12.5 g of 3-amino-1,2,4-benzotriazine-1,4-di-N-oxide (71% of theory) separates out in the form of reddish-golden crystals which melt, with decomposition, at 220°C.

Analysis $C_7H_6N_4O_2$ (178): Calculated: C 47.3%, H 3.4%, N 31.4%. Found: C 47.2%, H 4.0%, N 30.1%.

On acidifying the mother liquor with acetic acid, a further 3.2 g (18% of theory) of 3-amino-1,2,4-benzotriazine-1,4-di-N-oxide are obtained and after recrystallization from dimethylformamide this material melts, with decomposition at 220°C.

Total yield: 89% of theory.

EXAMPLE 2

In a fashion analogous to that set forth in Example 1, 5-chlorobenzofuroxan is allowed to react with disodium cyanamide to yield a mixture of 6-chloro and 7-chloro-3-amino-1,2,4-benzotriazine-1,4-di-N-oxide in the form of red crystals, m.p. 280°C (dec).

EXAMPLE 3

In a fashion analogous to that set forth in Example 1, 5-methylbenzofuroxan is allowed to react with disodium cyanamide to yield a mixture of 6-methyl and 7-methyl-3-amino-1,2,4-benzotriazine-1,4-di-N-oxide in the form of brown-red crystals, m.p. 145°C (dec).

EXAMPLE 4

In a fashion analogous to that set forth in Example 1, 5-methoxybenzofuroxan is allowed to react with disodium cyanamide to yield a mixture of 6-methoxy and 7-methoxy-3-amino-1,2,4-benzotriazine-1,4-di-N-oxide in the form of red crystals, m.p. 220°C (dec).

EXAMPLE 5

In a fashion analogous to that set forth in Example 1, 5-ethoxybenzofuroxan is allowed to react with disodium cyanamide to yield a mixture of 6-ethoxy and 7-ethoxy-3-amino-1,2,4-benzotriazine-1,4-di-N-oxide in the form of orange-red crystals, m.p. 202°C (dec).

EXAMPLE 6

In a similar fashion, utilizing 5,6-dimethylbenzofuroxan and 5,6-dichlorobenzofuroxan, there are respectively obtained 3-amino-6,7-dimethyl-1,2,4-benzotriazine-1,4-di-N-oxide and 3-amino-6,7-dichloro-1,2,4-benzotriazine-1,4-di-N-oxide.

Likewise the following 5-substituted benzofuroxans can be employed to yield a mixture of the corresponding 6-and 7-substituted 3-amino-1,2,4-benzotriazine-1,4-di-N-oxides:
5-ethylbenzofuroxan
5-fluorobenzofuroxan
5-bromobenzofuroxan
5-carbonamidobenzofuroxan
5-carboxybenzofuroxan
5-sulfonamidobenzofuroxan
5-(pentafluoroethyl)benzofuroxan
5-(dichloromethyl)benzofuroxan, and
5-(dichlorofluoromethyl)benzofuroxan.

Similarly benzofuroxans which are disubstituted by different groups can be analogously utilized. Thus 5-chloro-6-methylbenzofuroxan, 5-methoxy-6-bromobenzofuroxan and 5-ethoxy-6-methylbenzofuroxan respectively yield an isomeric mixture of 3-amino-6-chloro-7-methyl-1,2,4-benzotriazine-1,4-di-N-oxide and 3-amino-6-methyl-7-chloro-1,2,4-benzotriazine-1,4-di-N-oxide; an isomeric mixture of 3-amino-6-methoxy-7-bromo-1,2,4-benzotriazine-1,4-di-N-oxide and 3-amino-6-bromo-7-methoxy-1,2,4-benzotriazine-1,4-di-N-oxide; and an isomeric mixture of 3-amino-6-ethoxy-7-methyl-1,2,4-benzotriazine-1,4-di-N-oxide and 3-amino-6-methyl-7-ethoxy-1,2,4-benzotriazine-1,4-di-N-oxide.

The growth promoting activity of the new compounds and their effectiveness in improving the fodder utilisation may be illustrated by the following data:

Test animals : chicken (kept in cages, with complete fodder and water ad libitum)

The active ingredient is mixed in a finely divided form to the fodder according to customary methods. The tests were performed with 12 animals in each tested group.

| Active ingredient: compound of Example 4 Concentration of the active ingredient in the fodder: 10 PPM (by weight) | | | |
|---|---|---|---|
| week | weight increase (all animals) in gram | Weight increase in relation to the control group (%) | Consumption of fodder in relation to the control group (%) |
| 0 | 75 | 100 | 100 |
| 1 | 148.4 | 102.8 | 85.7 |
| 2 | 276.7 | 109.0 | 90.4 |
| 3 | 475.0 | 105.8 | 93.4 |
| 4 | 761.8 | 110.4 | 98.5 |
| 5 | 1019.1 | 106.4 | 101.1 |
| 6 | 1296.4 | 106.0 | 92.2 |

What is claimed is:

1. A pharmaceutical composition useful for the treatment of bacterial infections in humans and animals which comprises an antibacterially effective amount of a compound of the formula:

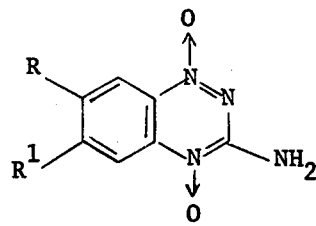

or an isomeric mixture thereof, wherein
R is hydrogen, halogeno, lower alkyl, halo(lower alkyl), lower alkoxy, carbamyl, sulfonamido, carboxy or carbo(lower alkoxy), and
$R^1$ is hydrogen, halogeno, lower alkyl, halo(lower alkyl), lower alkoxy, carbamyl, sulfonamido, carboxy or carbo(lower alkoxy),
in combination with a pharmaceutically acceptable nontoxic inert diluent or carrier.

2. A composition according to claim 1 wherein one of R and $R^1$ is hydrogen, halogeno, lower alkyl, halo(lower alkyl), lower alkoxy, carbamyl, sulfonamido, carboxy or carbo(lower alkoxy) and the other of R and $R^1$ is halogeno, lower alkyl, halo(lower alkyl), lower alkoxy, carbamyl, sulfonamido, carboxy or carbo(lower alkoxy).

3. A composition according to claim 1 wherein
a. R and $R^1$ are each hydrogen;
b. one of R and $R^1$ is hydrogen and the other is chloro, fluoro, bromo, methyl, ethyl, methoxy, ethoxy, dichloromethyl, dichlorofluoromethyl, pentafluoromethyl, carbonamido, sulfonamido or carboxy;
c. R and $R^1$ are each methyl or chloro;
d. one of R and $R^1$ is chloro and the other is methyl;
e. one of R and $R^1$ is methoxy and the other is bromo; or
f. one of R and $R^1$ is methyl and the other is ethoxy.

4. A composition according to claim 1 wherein said compound is an isomeric mixture of:
a. a compound of the formula:

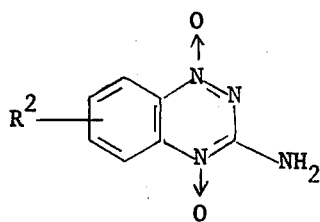

wherein $R^2$ is in the 6- or 7-position and is selected from the group consisting of chloro, bromo, fluoro, methyl, ethyl, methoxy, ethoxy, dichloromethyl, dichlorofluoromethyl, pentafluoroethyl, carboxy, carbonamido or sulfonamido, the $R^2$ radicals in the mixture being identical; or
b. an isomeric mixture of (1) 3-amino-6-chloro-7-methyl-1,2,4-benzotriazine-1,4-di-N-oxide and 3-amino-6-methyl-7-chloro-1,2,4-benzotriazine-1,4-di-N-oxide; (2) 3-amino-6-methoxy-7-bromo-1,2,4-benzotriazine-1,4-di-N-oxide and 3-amino-6-bromo-7-methoxy-1,2,4-benzotriazine-1,4-di-N-oxide; or (3) 3-amino-6-ethoxy-7-methyl-1,2,4-benzotriazine-1,4-di-N-oxide and 3-amino-6-methyl-7-ethoxy-1,2,4-benzotriazine-1,4-di-N-oxide.

5. A composition according to claim 1 wherein the compound is 3-amino-1,2,4-benzotriazine-1,4-di-N-oxide.

6. A composition according to claim 1 wherein the compound is a mixture of 6-chloro and 7-chloro-3-amino-1,2,4-benzotriazine-1,4-di-N-oxide.

7. A composition according to claim 1 wherein the compound is a mixture of 6-methyl and 7-methyl-3-amino-1,2,4-benzotriazine-1,4-di-N-oxide.

8. A composition according to claim 1 wherein the compound is a mixture of 6-methoxy and 7-methoxy-3-amino-1,2,4-benzotriazine-1,4-di-N-oxide.

9. A composition according to claim 1 wherein the compound is a mixture of 6-ethoxy and 7-ethoxy-3-amino-1,2,4-benzotriazine-1,4-di-N-oxide.

10. A composition according to claim 1 wherein the compound is 3-amino-6,7-dimethyl-1,2,4-benzotriazine-1,4-di-N-oxide.

11. A composition according to claim 1 wherein the compound is 3-amino-6,7-dichloro-1,2,4-benzotriazine-1,4-di-N-oxide.

12. A composition according to claim 1 wherein the compound is an isomeric mixture of 3-amino-6-chloro-7-methyl-1,2,4-benzotriazine-1,4-di-N-oxide and 3-amino-6-methyl-7-chloro-1,2,4-benzotriazine-1,4-di-N-oxide.

13. A composition according to claim 1 wherein the compound is an isomeric mixture of 3-amino-6-methoxy-7-bromo-1,2,4-benzotriazine-1,4-di-N-oxide and 3-amino-6-bromo-7-methoxy-1,2,4-benzotriazine-1,4-di-N-oxide.

14. A composition according to claim 1 wherein the compound is an isomeric mixture of 3-amino-6-ethoxy-7-methyl-1,2,4-benzotriazine-1,4-di-N-oxide and 3-amino-6-methyl-7-ethoxy-1,2,4-benzotriazine-1,4-di-N-oxide.

15. A composition according to claim 1 in oral administration form.

16. A composition according to claim 1 in parenteral administration form.

17. A composition according to claim 1 in topical application form.

18. A method of treating bacterial infections in humans and animals which comprises administering to such human or animal an antibacterially effective amount of a compound of the formula:

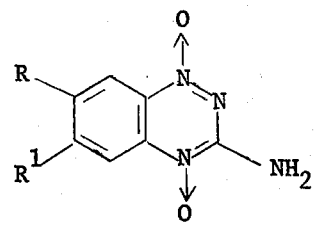

or an isomeric mixture thereof, wherein
R is hydrogen, halogeno, lower alkyl, halo(lower alkyl), lower alkoxy, carbamyl, sulfonamido, carboxy or carbo(lower alkoxy), and
$R^1$ is hydrogen, halogeno, lower alkyl, halo(lower alkyl), lower alkoxy, carbamyl, sulfonamido, carboxy or carbo(lower alkoxy).

19. A method according to claim 18 wherein one of R and $R^1$ is hydrogen, halogeno, lower alkyl, halo(lower alkyl), lower alkoxy, carbamyl, sulfonamido, carboxy or carbo(lower alkoxy) and the other of R and $R^1$ is halogeno, lower alkyl, halo(lower alkyl), lower alkoxy, carbamyl, sulfonamido, carboxy or carbo(lower alkoxy).

20. A method according to claim 18 wherein
a. R and $R^1$ are each hydrogen;
b. one of R and $R^1$ is hydrogen and the other is chloro, fluoro, bromo, methyl, ethyl, methoxy, ethoxy, dichloromethyl, dichlorofluoromethyl, pentafluoromethyl, carbonamido, sulfonamido or carboxy;
c. R and $R^1$ are each methyl or chloro;
d. one of R and $R^1$ is chloro and the other is methyl;
e. one of R and $R^1$ is methoxy and the other is bromo; or
f. one of R and $R^1$ is methyl and the other is ethoxy.

21. A method according to claim 18 wherein said compound is an isomeric mixture of:
a. a compound of the formula:

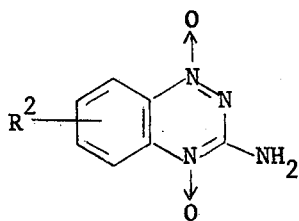

wherein R² is in the 6- or 7-position and is selected from the group consisting of chloro, bromo, fluoro, methyl, ethyl, methoxy, ethoxy, dichloromethyl, dichlorofluoromethyl, pentafluoroethyl, carboxy, carbonamido or sulfonamido, the R² radicals in the mixture being identical; or b. an isomeric mixture of (1) 3-amino-6-chloro-7-methyl-1,2,4-benzotriazine-1,4-di-N-oxide and 3-amino-6-methyl-7-chloro-1,2,4-benzotriazine-1,4-di-N-oxide; (2) 3-amino-6-methoxy-7-bromo-1,2,4-benzotriazine-1,4-di-N-oxide and 3-amino-6-bromo-7-methoxy-1,2,4-benzotriazine-1,4-di-N-oxide; or (3) 3-amino-6-ethoxy-7-methyl-1,2,4-benzotriazine-1,4-di-N-oxide and 3-amino-6-methyl-7-ethoxy-1,2,4-benzotriazine-1,4-di-N-oxide.

22. A method according to claim 18 wherein the compound is 3-amino-1,2,4-benzotriazine-1,4-di-N-oxide.

23. A method according to claim 18 wherein the compound is a mixture of 6-chloro and 7-chloro-3-amino-1,2,4-benzotriazine-1,4-di-N-oxide.

24. A method according to claim 18 wherein the compound is a mixture of 6-methyl and 7-methyl-3-amino-1,2,4-benzotriazine-1,4-di-N-oxide.

25. A method according to claim 18 wherein the compound is a mixture of 6-methoxy and 7-methoxy-3-amino-1,2,4-benzotriazine-1,4-di-N-oxide.

26. A method according to claim 18 wherein the compound is a mixture of 6-ethoxy and 7-ethoxy-3-amino-1,2,4-benzotriazine-1,4-di-N-oxide.

27. A method according to claim 18 wherein the compound is 3-amino-6,7-dimethyl-1,2,4-benzotriazine-1,4-di-N-oxide.

28. A method according to claim 18 wherein the compound is 3-amino-6,7-dichloro-1,2,4-benzotriazine-1,4-di-N-oxide.

29. A method according to claim 18 wherein the compound is an isomeric mixture of 3-amino-6-chloro-7-methyl-1,2,4-benzotriazine-1,4-di-N-oxide and 3-amino-6-methyl-7-chloro-1,2,4-benzotriazine-1,4di-N-oxide.

30. A method according to claim 18 wherein the compound is an isomeric mixture of 3-amino-6-methoxy-7-bromo-1,2,4-benzotriazine-1,4-di-N-oxide and 3-amino-6-bromo-7-methoxy-1,2,4-benzotriazine-1,4-di-N-oxide.

31. A method according to claim 18 wherein the compound is an isomeric mixture of 3-amino-6-ethoxy-7-methyl-1,2,4-benzotriazine-1,4-di-N-oxide and 3-amino-6-methyl-7-ethoxy-1,2,4-benzotriazine-1,4-di-N-oxide.

32. A method according to claim 18 wherein the administration is oral.

33. A method according to claim 18 wherein the administration is parenteral.

34. A method according to claim 18 wherein the administration is by topical application.

* * * * *